United States Patent
Murali (10) Patent No.: US 11,293,004 B2
(45) Date of Patent: Apr. 5, 2022

(54) BENCHTOP INCUBATOR INCLUDING MULTIPLE TEMPERATURE MONITORS

(71) Applicant: SciTech Consultants, LLC, Orangeburg, SC (US)

(72) Inventor: Anuradha Murali, Orangeburg, SC (US)

(73) Assignee: SciTech Consultants, LLC, Orangeburg, SC (US)

( * ) Notice: Subject to any disclaimer, the term of this patent is extended or adjusted under 35 U.S.C. 154(b) by 838 days.

(21) Appl. No.: 15/865,331

(22) Filed: Jan. 9, 2018

(65) Prior Publication Data

US 2019/0211300 A1 Jul. 11, 2019

(51) Int. Cl.
| | | |
|---|---|---|
| *C12M 1/00* | (2006.01) | |
| *C12M 3/00* | (2006.01) | |
| *B01L 7/00* | (2006.01) | |
| *G01N 1/44* | (2006.01) | |

(52) U.S. Cl.
CPC .............. *C12M 41/14* (2013.01); *B01L 7/52* (2013.01); *C12M 23/48* (2013.01); *B01L 2300/0627* (2013.01); *B01L 2300/0809* (2013.01); *B01L 2300/18* (2013.01); *G01N 1/44* (2013.01)

(58) Field of Classification Search
CPC .. B01L 1/025; B01L 2200/02; B01L 2300/06; B01L 2300/0627; B01L 2300/0809; B01L 2300/0822; B01L 2300/0829; B01L 2300/18; B01L 7/52; B01L 9/523; C12M 23/48; C12M 41/14; G01N 1/44
See application file for complete search history.

(56) References Cited

U.S. PATENT DOCUMENTS

| | | | |
|---|---|---|---|
| 1,598,585 | A | 8/1926 | Almendinger |
| 2,364,722 | A | 12/1944 | Kazantzeff |
| 2,505,360 | A | 4/1950 | Jeffreys |
| 3,712,268 | A | 1/1973 | Reed |
| 3,746,161 | A | 7/1973 | Jones |

(Continued)

FOREIGN PATENT DOCUMENTS

| | | |
|---|---|---|
| EP | 2484750 | 8/2012 |
| EP | 3255137 | 12/2017 |

(Continued)

OTHER PUBLICATIONS

Biogene Multi Room Incubator (XP-002790814) and Dual Chamber Incubator (XP-002790601) *Biotechnologies, Inc.* www.biotechnologies.com.

(Continued)

*Primary Examiner* — Lydia Edwards
(74) *Attorney, Agent, or Firm* — Dority & Manning, P.A.

(57) ABSTRACT

A bench top incubator is described. The bench top incubator includes a multiple temperature sensors and control systems so as to provide independent data logs of temperature data from each of the multiple temperature sensors. The incubator is relatively simple and small in design and can be conveniently located to carry out temperature processing of biological samples such as fixed cells and tissues, biological fluids, and so forth. The incubator can also include multiple tray stacks, each tray stack configured to retain either microscope slides or well plates

17 Claims, 6 Drawing Sheets

(56) References Cited

U.S. PATENT DOCUMENTS

| | | | |
|---|---|---|---|
| 4,689,303 A | 8/1987 | Kraft et al. | |
| 5,266,272 A | 11/1993 | Griner et al. | |
| 5,525,512 A | 6/1996 | Pieler et al. | |
| 5,577,821 A | 11/1996 | Chu | |
| 5,985,653 A | 11/1999 | Armstrong et al. | |
| 6,238,031 B1 | 5/2001 | Weng | |
| 6,238,032 B1 | 5/2001 | Cooper et al. | |
| 6,258,325 B1 | 7/2001 | Sanadi | |
| 6,271,022 B1 | 8/2001 | Bochner | |
| 6,367,900 B1 | 4/2002 | Woerner | |
| 6,465,242 B1 | 10/2002 | Kanipayor et al. | |
| 7,029,080 B2 | 4/2006 | Barry, Jr. et al. | |
| 7,112,241 B2 | 9/2006 | Sha | |
| 8,511,765 B1 | 8/2013 | Chen et al. | |
| 2003/0031602 A1 | 2/2003 | Weselak et al. | |
| 2003/0092178 A1* | 5/2003 | Yerden | C12M 41/32 435/375 |
| 2006/0093514 A1 | 5/2006 | Dawes | |
| 2007/0217964 A1 | 9/2007 | Johnson et al. | |
| 2010/0112577 A1 | 5/2010 | Chu | |
| 2010/0291664 A1 | 11/2010 | Herbert et al. | |
| 2010/0315628 A1 | 12/2010 | Mertsching et al. | |
| 2011/0183411 A1 | 7/2011 | Nichols et al. | |
| 2013/0050692 A1 | 2/2013 | Tang et al. | |
| 2015/0299639 A1 | 10/2015 | Kleefstra et al. | |
| 2017/0073628 A1 | 3/2017 | Zander et al. | |
| 2017/0348693 A1 | 12/2017 | Murali | |

FOREIGN PATENT DOCUMENTS

| | | |
|---|---|---|
| KR | 10-2011-0122291 | 11/2011 |
| WO | WO 2007/120619 | 10/2007 |
| WO | WO 2017/214087 | 12/2017 |

OTHER PUBLICATIONS

EPO Extended European Search Report—Appl. No. 19150911.6 (dated May 10, 2019).

* cited by examiner

BENCHTOP INCUBATOR INCLUDING MULTIPLE TEMPERATURE MONITORS

BACKGROUND

The incubation of fixed cells and other non-living biological samples at designated conditions is common in a large variety of molecular and biological techniques such as immunohistochemistry, immunocytochemistry, enzyme-linked immunosorbent assay (ELISA), in situ reverse transcription polymerase chain reaction (RT-PCR), and so forth. Such incubation is in many ways simpler than incubation of live cells. For instance, incubation of fixed cells does not require sterile incubation conditions or highly specific gaseous atmospheric control (e.g., $CO_2$ control).

Unfortunately, the relatively simpler processes of such incubations leads to incubation protocols that have lower reproducibility and therefore less result confidence. For instance, when incubating at room temperature, fixed cell systems (e.g., plates or slides) are simply held at whatever "room temperature" may be in that particular laboratory, which can vary widely from one laboratory to another. Issues also exist for lower and higher temperature non-live cell incubation systems. Lower temperature incubation is generally carried out by simply placing the samples in a laboratory refrigerator that is very rarely (if ever) calibrated and very rarely includes a temperature log. Higher temperature incubations are similarly carried out by use of a warm room that is neither calibrated nor logged. Moreover, even if an incubation area is properly calibrated, variations to the system over the course of a protocol, e.g., opening of the incubator door, removal of a sample to make observations, air currents throughout a large enclosure, etc., can alter the temperature of the sample over the course of the incubation period. Unfortunately, even small variations in temperature throughout a procedure can affect outcomes, with a lack of accurate temperature data over the course of the incubation period negatively affecting reproducibility and outcome confidence.

What is needed in the art is an incubator that can provide for accurate temperature logging for multiple biological samples, for instance multiple samples being examined by use of different examination protocols. An incubator having multiple temperature logging capability that can improve reproducibility of laboratory protocols and that is less expensive, smaller, and more user-friendly would be of great benefit in the art.

SUMMARY

According to one embodiment, disclosed is a bench top incubator configured for use with biological systems (e.g., fixed cells or tissues, serum, biological fluids, etc.). The benchtop incubator can include first and second tray stacks and first and second temperature sensors. The bench top incubator also includes a temperature control system and a data logger in communication with the control system. The control system is configured to generate an incubation temperature in a thermally isolated chamber of the incubator and thereby control the temperature of the samples retained within the chamber. The control system is also configured to obtain temperature data from the temperature sensors located within the incubator (e.g., at each tray stack within the incubator) over the course of an incubation protocol and communicate that data to the data logger, which is configured to provide an independent data log for each of the temperature sensors. The control system can also include timing circuitry that can be used to vary the chamber temperature over the course of a protocol and/or obtain temperature data at predetermined intervals.

The tray stacks can be configured to retain samples of different types. For instance, the first tray stack can be configured to retain a plurality of vertically stacked slide trays, with each slide tray comprising one or more slide insets. Each slide inset can be sized to retain an individual microscope slide. The second tray stack can be configured to retain a plurality of vertically stacked plate trays, each of which including an inset configured to retain a multi-well plate, e.g., a 96-well plate. In one embodiment, the tray stacks can be thermally isolated from one another, allowing for independent temperature control of the different tray stacks and of different samples.

Also disclosed are methods for utilizing the incubators. For example, a method can include locating a first biological sample on a first tray stack within the incubator and locating a second biological sample on a second tray stack within the incubator. The method can also include programming a temperature control assembly such that temperature data from first and second temperature sensors is communicated to a data logger. The first and second temperature sensors provide data from areas encompassing the first and second biological samples, respectively. A data log of the temperature data from each temperature sensor can then be provided. The data log can also provide minimum and maximum temperatures over the course of each defined enquiry period for each temperature sensor. For instance, a temperature at a particular enquiry time (T) as well as a maximum temperature ($T_{max}$) and a minimum temperature ($T_{min}$) over an enquiry time period that encompasses the particular enquiry time can be obtained from each of the temperature sensors. This process can then be repeated over a plurality of enquiry time periods (e.g., every minute) over the course of an entire protocol. The data from each enquiry time period (T, $T_{min}$, $T_{max}$) can then be logged throughout a protocol. Optionally, the system can also log temperatures of the environment external to the incubator (e.g., external temperature as well as minimum and maximum external temperature over each enquiry period).

BRIEF DESCRIPTION OF THE DRAWINGS

A full and enabling description of the present disclosure, including the best mode thereof, to one of ordinary skill in the art, is set forth more particularly in the remainder of the specification, including reference to the accompanying figures in which.

Repeat use of reference characters in the present specification and drawings is intended to represent the same or analogous features or elements of the present invention.

DETAILED DESCRIPTION

Reference now will be made in detail to embodiments of the disclosure, one or more examples of which are set forth below. Each example is provided by way of explanation, not limitation of the disclosed subject matter. In fact, it will be apparent to those skilled in the art that various modifications and variations can be made in the present disclosure without departing from the scope or spirit of the subject matter. For instance, features illustrated or described as part of one embodiment, can be used on another embodiment to yield a still further embodiment.

The present disclosure is generally directed to a bench top incubator that can be utilized in a wide variety of research activities with improved accuracy and reliability. More specifically, the bench top incubators disclosed herein can include multiple temperature sensors within the incubator and a control system in communication with the multiple temperature sensors so as to accurately log temperature at multiple locations within the incubator over the course of an incubation protocol. Beneficially, as the incubators include multiple temperature sensors, data for different areas both within and external to the incubators can be obtained, leading to increased accuracy. For example, in one embodiment, an incubator can accommodate both microscope slides and multi-well plates in different areas of the incubator, and the control system can independently obtain and log temperature data for each area.

Figure 1:
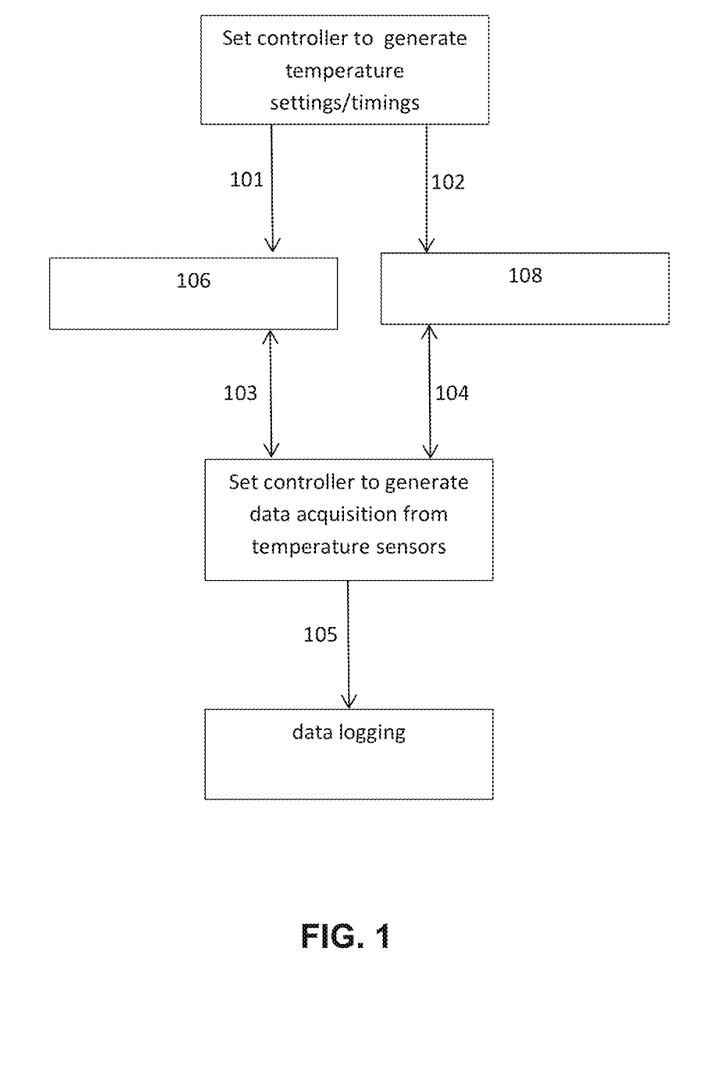
FIG. 1 illustrates a flow diagram for use of a bench top incubator as described herein.

FIG. 1 provides a flow diagram for one embodiment of an incubator system disclosed herein. As shown, the incubator can include a controller and two distinct areas 106, 108, each of which being in communication with the controller. The controller can generate a desired temperature at each area 106, 108 via a heating/cooling system as indicated by communication lines 101, 102. Depending upon the specific design of the incubator, the control system can generate the same temperature at each area 106, 108 or, in those embodiments in which the areas are thermally isolated from one another, the control system can generate a different temperature at each area 106, 108. Each of the areas 106, 108 can also include at least one temperature sensor, and the controller can request and obtain temperature data from the temperature sensors as indicated by communication lines 103, 104. The temperature data obtained by the controller can then be used to maintain the desired temperature and also can be communicated 105 to a data logger, which can provide an independent data log for each temperature sensor. The data log can be communicated, either in real time or at a later time, e.g., upon request by a user.

Figure 2:
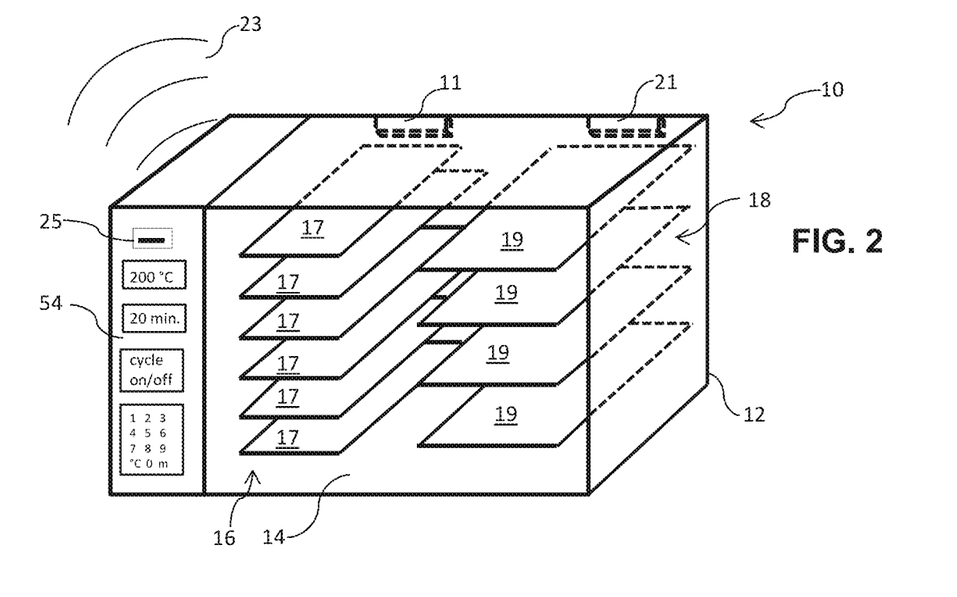
FIG. 2 schematically illustrates one embodiment of a bench top incubator as described herein.

FIG. 2 illustrates one embodiment of a bench top incubator 10 as encompassed herein. The incubator 10 includes a housing 12 that defines an interior chamber 14 that can be thermally isolated from the surrounding environment. The chamber 14 is configured to retain therein a first tray stack 16 and a second tray stack 18. The first tray stack 16 can include a plurality of slide trays 17, each of which being configured to retain one or more microscope slides, and the second tray stack 18 can include a plurality of plate trays 19, each of which being configured to retain one or more multi-well plates. As illustrated, the slide trays 17 and the plate trays 19 are not of the same dimensions as one another, but this is not a requirement of the bench top incubator.

A bench top incubator can also include a temperature control assembly 54 that can be used to generate and monitor temperature within the chamber 14. A temperature control assembly 54 can be operatively coupled with the housing 12 to control the temperature within the chamber 14 so that the temperature remains within a desired range. For example, in one application, the control assembly 54 can maintain the temperature within the chamber 14 at a predetermined temperature of from about 2° C. to about 150° C. with high accuracy, for instance such that the chamber temperature is maintained within a range of the predetermined temperature of about ±1.0° C., ±0.5° C., or ±0.2° C.

A temperature control assembly 54 can include components as are generally known in the art for generating the predetermined temperature within the chamber 14 including a heater and/or a cooler in communication with the controller. A heater and/or cooler can be positioned between the outer walls and the inner walls of the housing 12 and are operable for heating or cooling the incubation chamber 14 to generate an internal temperature in the incubator 10 according to the settings/timings input to the controller. The heater and/or cooler may be any conventional device as known in the art. By way of example, a heater can include a low watt density, high surface area, contact resistive heater.

The temperature system 54 can include a controller that can direct electrical power from a power supply (not shown) to cycle the heater/cooler. The controller may be any conventional programmable microprocessor device. In one embodiment, the temperature control system may be coupled to a timer according to conventional methodology so as to control the timing of an incubation within the chamber(s). By way of example, in one embodiment and without limitation, the control system 54 can include a controller, e.g., a micro-controller, that can include built in analog-to-digital circuitry, built in input/output circuitry, timing circuitry, and a built in serial communications controller. The controller can interface with a pre-programmed electrically erasable and programmable read only memory (EEPROM).

The incubator 10 can also include multiple temperature sensors that can be located in different areas of the incubator chamber 14 and that are in communication with the controller. For instance, in the illustrated embodiment, the incubator 10 includes a first temperature sensor 11 that is located in the general area of the first tray stack 16 and a second temperature sensor 21 that is located in the general area of the second tray stack 18. In the illustrated embodiment, the temperature sensors 11, 21, are located at the upper end of the tray stacks 16, 18, but it should be understood that these particular locations of the temperature sensors are not required and temperature sensors can be located at any location within an incubator chamber so as to obtain the temperature of the surrounding area. For instance, a first temperature sensor can be located in the midst of a tray stack (e.g., on a middle tray), on either end of a tray stack, on any side of a tray stack, or within a tray stack. In one embodiment, a plurality of temperature sensors can be associated with each tray stack, so as to obtain temperature data over multiple areas of an incubator chamber. Moreover, a system can also include one or more temperature sensors external to the incubator chamber 14, for instance in order to obtain temperature data of the surrounding area external to the incubator.

The proximity of each temperature sensor to the heater/cooler, in combination with the constrained volume of the chamber 14 and the area for which each temperature sensor is designed to provide data, can allow the temperature control assembly 54 to maintain the targeted temperature within the chamber 14 as well as to obtain data concerning the temperature within the chamber 14 over time.

A temperature sensor 11, 21 can be of any suitable design. For instance a temperature sensor 11, 21 can incorporate a thermocouple and an electronic circuit to receive and transmit signals between the thermocouple and the controller. As such, the controller can also contain control instructions and sensor drivers for the multiple sensors plus data storage and communication for storing and communicating data from each sensor. The controller can accept input from a real-time clock, the temperature sensors, and analog signal conditioning bandpass filters to control the temperature within the chamber 14 as well as to acquire temperature data over the course of an incubation.

The controller can also include a receiver/transmitter mechanism that can convey the temperature data acquired from the multiple temperature sensors to an internal or external data logger and optionally from the data logger to a data receiver. The data logger can be internal or external to the incubator and can function as a repository for the temperature data. As such the data logger can accommodate the data streams of the multiple temperature sensors conveyed via the receiver/transmitter mechanism.

Temperature data compiled, stored, and/or communicated by the data logger can include measured temperatures at predetermined time periods, maximum and minimum temperatures within predetermined time periods, rates of change of temperatures within the incubator, external temperature (i.e., room temperature external to the incubator), and so forth. For instance, a series of enquiry time periods can be defined over the course of a protocol that can be of any desired period (e.g., one minute, two minutes, five minutes, ten minutes, etc.). The data logger can then compile, store and/or communicate temperature data from each enquiry time period that can include, for example and without limitation to, a single representative temperature within the time period (e.g., at the mid-point of the period), a maximum temperature ($T_{max}$) registered over the time period, a minimum temperature ($T_{min}$) registered over the time period.

Temperature data can be transmitted from the temperature sensors to the data logger either wirelessly or by hard wiring. For instance, in those embodiments in which the data logger is external, the temperature sensors can transmit the data to the data logger via Bluetooth technology (e.g., Bluetooth Low Energy technology), infrared line of sight signal, radio frequency communication techniques, or any other wireless connection (e.g., WLAN).

The data logger can store the temperature data and can transmit the temperature logs in real time or upon request either wirelessly or by hard wiring. For example, in one embodiment the system can include a data interface and a radio unit which allows the establishment of a wireless connection (WLAN) 23 to a computer network. Alternatively or in addition to a wireless connection capability, the system can include a port 25 that provides for wired access to the information collected and logged by the data logger. Data can also be transmitted from the data logger via other wireless technologies as known in the art, e.g., Bluetooth technology. As such, a system can communicate the data logs to a receiving unit, which can include, e.g., a monitor and display system to monitor and display the temperature data either in real time (e.g., as the data log is developed) or at a later time (e.g., as the complete data log over the predetermined time course), as desired. The data logger can optionally communicate with personal communications devices, e.g., smart phones, personal computers, laptop computers, electronic notebooks, etc. through text, e-mail, specific communications applications, or any other communications technology that can be designed for the data logger. For instance, in one embodiment, the data logger can communicate actionable information, e.g., if the temperature in the incubator goes outside of a preset range, as an alarm to a communications device (e.g., a phone). The data logger can include software and processing and communications capability to communicate entire data logs or particular items (e.g., completion of a data cycle) automatically or upon request.

The data logger can include a processor-controlled storage unit that is configured to receive data from each of the temperature sensors via a wired or wireless interface between the two and store the temperature data for each sensor separately. The data logger can be controlled by the microprocessor of the temperature control system and can include a storage medium, at least one interface and a plurality of channels for connecting to each of the multiple temperature sensors. The specific design of the data logging program can be varied and can depend on the particular incubation protocol and desired enquiry time interval for the temperature data as well as the time interval for storage of the temperature data, e.g., periodic or continual. For instance, the storage of the temperature data may be carried out at intervals (e.g., a data dump including data from multiple enquiry time periods) or in real time at the time of the respective data generation. In any event, the storage process can be fully automatic.

In one embodiment, the data logger of the temperature control assembly 54 can have multiple modes of operation including a timed mode, an event driven mode and a continuous mode. Alternatively, the data logger can include only one or two of such operation modes.

When operating in a timed mode, the controller can write the value of each temperature sensor to the EEPROM according to the time interval programmed into the controller. Beneficially, the enquiry time interval (also referred to as an enquiry time period herein) for each temperature sensor and associated data log need not be identical to one another. For example, if the predetermined enquiry time interval for temperature sensor 11 is set to 60 seconds, then every 60 seconds, the controller can convey the data (e.g., T, $T_{max}$, $T_{min}$) from temperature sensor 11 to the data log for that temperature sensor. The timed logging process can continue for the entire pre-set time interval. Following data collection or in real-time, the data of the data log can be conveyed, via connection at port 25 (e.g., a USB port) or wirelessly via a WLAN or Bluetooth signal 23 to an external device. Data collection for a second temperature sensor 21 can be set to the same timing as the first temperature sensor 11 or data logging for the second temperature sensor can operate in a different timed mode, as desired. In one embodiment, the data logging for the different temperature sensors can operate in different modes, e.g., the data log for temperature sensor 11 can be according to a timed mode and the data log for temperature sensor 21 can be according to an event driven mode.

In an event driven mode, a temperature sensor 11 can obtain data continuously (e.g., at a sample rate of approximately 5 kHz) and send that data to the controller. The controller can compare the value to a programmed threshold. If the value is greater than the threshold value, then the controller can communicate the value of the temperature sensor and communicates the value to the data logger. The event driven mode can be useful for determining when and to what degree the temperature of the area went beyond threshold limits in order to, e.g., send an alarm to an external device.

In a continuous mode, the data from the temperature sensors is continuously delivered to the data logger and a continuous record of the temperature at the temperature sensor can be recorded.

In addition to the data logger and the associated process control components, the temperature control assembly 54 can include input/output capabilities as are known in the art, e.g., timing inputs, temperature inputs, current temperature read out, etc. In one embodiment, the temperature control system 54 can include and alarm system to provide an alarm when the temperature of one or more of the temperature sensors is outside a selected range. An alarm can be audible, visual or any other suitable means or combination thereof and, as discussed previously, can be conveyed to an external device, e.g., via Bluetooth.

Data can be provided to an external device in any format. For instance, in one embodiment, the data logger can include software to convert the raw data to a desired output format, e.g., as an Excel® spreadsheet showing each time period as well as T, $T_{max}$, and $T_{min}$ for each period, or the like.

In one embodiment the bench top incubator can include multiple chambers that are thermally isolated from one another. For instance, in the embodiment illustrated in FIG. 3, the incubator 110 can include a first chamber 114 and a second chamber 115 that are thermally isolated from one another. In this embodiment, the first tray stack 16 including the slide trays 17 can be retained within the chamber 115. In addition the chamber 115 can include a first temperature sensor 111. The second tray stack 18 including the plate trays 19 can be retained within the chamber 114, and the chamber 114 can include a second temperature sensor 121.

Figure 3:
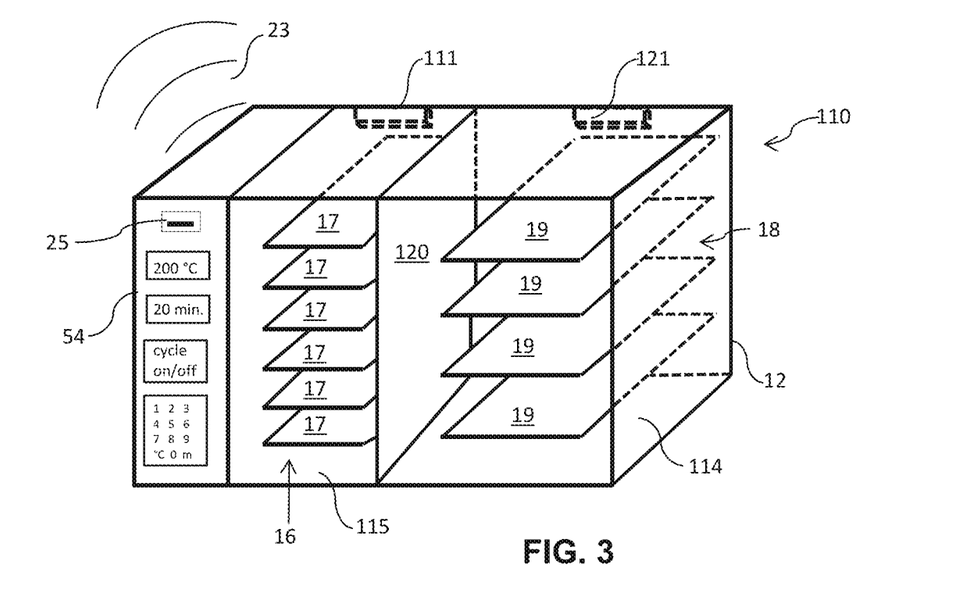
FIG. 3 schematically illustrates another embodiment of a bench top incubator including thermally isolated tray stacks.

The chambers 114, 115 can be separated from one another by a thermally insulating wall as is known in the art. For example, a thermally insulating wall 120 can include a first and second wall with an insulative material there between, as described above with regard to the outer housing of an incubator. In this embodiment, the controller of the temperature control assembly 154 can be used to generate a different temperature in each isolated chamber 114, 115. The independent data recording of each temperature sensor 111, 121, can generally be as described above.

It should be understood that a bench top incubator as disclosed herein is not intended to be limited to any particular number of tray stacks, any particular number of trays within each tray stack, or any particular number of temperature sensors. However, the bench top incubator is generally understood to be relatively small, so as to be portable and stable when located on a typical bench top. For instance, the housing 12 can generally be about 1.5 cubic meter (1.5 m³) or less in outer volume. In one embodiment, each outer dimension of the housing can be about 1.5 meter or less. Moreover the temperature control assembly 54, including a controller, temperature sensors, data logger(s) and associated control and communications components can be integral to the incubator, to maintain the ease in set-up and portability of the system.

Housing 12 can include an access door (not shown on FIG. 2 or FIG. 3), that can generally be disposed in a forwardly facing panel of the housing 12, but could as well be located in other panels of the housing 12, provided it allows access to the tray stacks within.

The housing 12 defines the thermally controlled chamber 14 for, e.g., culturing of fixed tissues or cells, biological fluids, serum etc. As such, the thermally controlled chamber 14 can include inner and outer spaced apart walls. The outer walls, inner walls and door can be formed of any suitable material such as, for example stainless steel, but may be manufactured from other suitable materials such as aluminum, ceramics, and/or high temperature plastic (e.g., acrylonitrile butadiene styrene (ABS)) as a matter of design choice. The walls surrounding the thermally controlled chamber 14 can include an insulation material within the surrounding walls as is generally known in the art such as expanded urethane.

The chamber 14 can be sized to hold two or more tray stacks 16, 18. By way of example, a chamber 14 can define an internal volume of about 1 m³ or less, about 0.75 m³ or less, or about 0.5 m³ or less in some embodiments. The small volume of the incubator chamber 14 can ensure improved temperature uniformity by positioning the plate trays 16, 18 at a consistent spacing from the inner walls.

Figure 4:
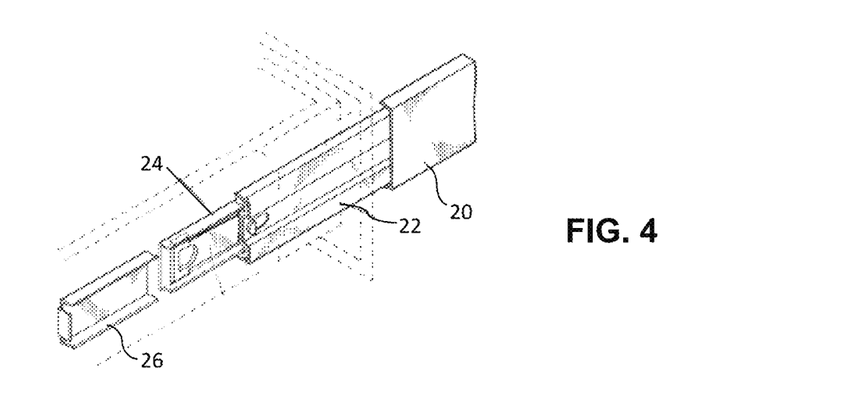
FIG. 4 illustrates one embodiment of a mounting bracket as may be utilized in conjunction with an individual tray of an incubator.

Each of the plate trays 17, 19 can be contained within the incubator chamber 14 in an accessible fashion by use of a suitable bracket or holding device as is generally known in the art. By way of example, and without limitation, FIG. 4 illustrates one typical sliding bracket that includes an outer rail 20, an intermediate rail 22, an inner rail 24, and a stop section 26. As shown, the various sections of the sliding bracket nest within one another and are slidingly engaged with one another. In use, a sliding bracket can be attached to either side of an individual tray 17, 19 (an example of which is shown in dashed lines in FIG. 4). When a single tray is drawn out to an accessible position, a pulling force can slide the sections 20, 22, 24, 26, out from one another as shown. A single tray can thus be pulled out, e.g., out of a door at the front of the chamber 14, for access. Similarly, by pushing against the stop section 26, the rails can telescope in and the tray can be returned to a storage space within the chamber.

Any suitable bracket system is incorporated herein, including immobile brackets that simply support the trays held thereon. Exemplary bracket systems include, without limitation, those described in U.S. Pat. No. 6,238,032 to Wend; U.S. Pat. No. 6,367,900 to Woerner; U.S. Pat. No. 7,029,080 to Barry, Jr., et al.; U.S. Pat. No. 8,511,765 to Chen, et al.; U.S. Pat. No. 5,577,821 to Chu; and U.S. Pat. No. 6,258,325 to Sanadi; all of which are incorporated herein by reference.

Figure 5:
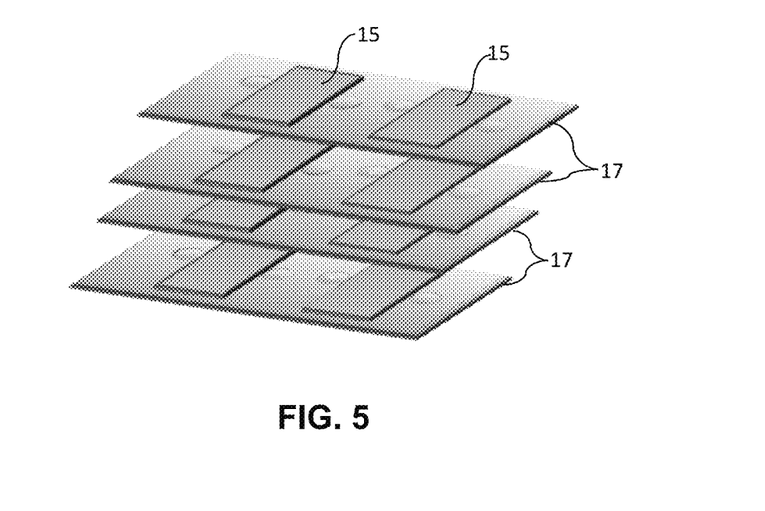
FIG. 5 schematically illustrates one embodiment of a tray stack including a plurality of vertically stacked slide trays.

FIG. 5 illustrates one example of a plurality of slide trays 17 as may form a tray stack 16. In the illustrated embodiment, each slide tray 17 is configured to retain two microscope slides 15, however, this is not a requirement of a bench top incubator, and a slide tray can be configured to retain 1, 2, 3, or more microscope slides.

Figure 6:
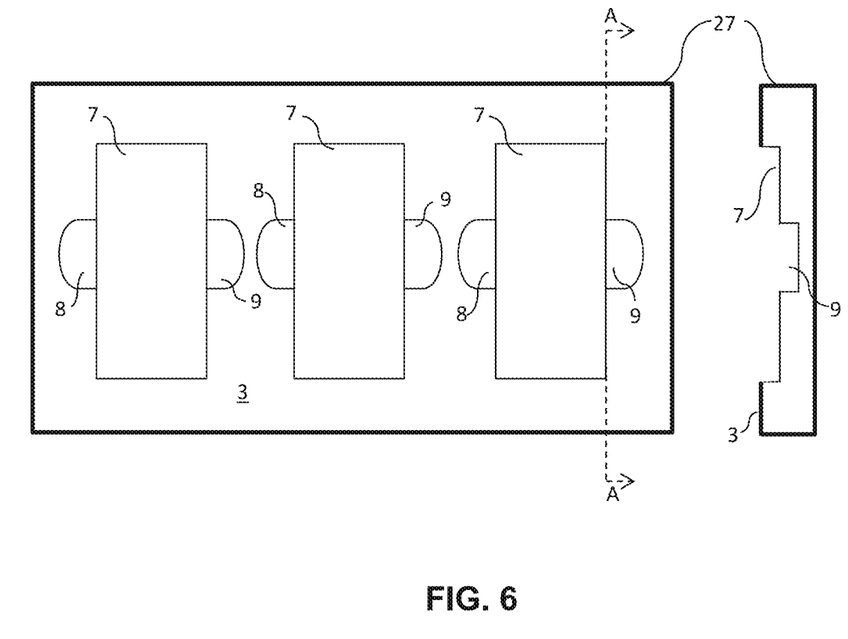
FIG. 6 schematically illustrates a top view and a side view of one embodiment of a slide tray.

A single slide tray 17 is illustrated in FIG. 6 including a top view (left) and a side view (right) taken along the line A-A. A slide tray 17 can be formed of any suitable material capable of withstanding expected conditions within an incubator. For instance, slide tray 17 can be formed of a suitable temperature stable plastic, e.g., acrylonitrile butadiene styrene (ABS), or the like and may be formed according to standard methods such as, without limitation, injection molding. A slide tray 17 can include suitable hardware as necessary to be retained in a chamber 14 by use of the desired bracket system.

In the embodiment of FIG. 6, the slide tray 27 is configured to retain three microscope slides at three slide insets 7. The slide insets 7 can generally be sized so as to retain a typical microscope slide, e.g., about 75 millimeters (mm) by about 26 mm in surface area and generally about 1 mm in height. An individual slide inset 7 can have any suitable depth (as seen in the side view of the slide tray 27) to retain a slide therein. The depth of a slide inset can be for instance about 2 mm or less, for example from about 0.1 mm to about 1.5 mm in some embodiments, or from about 0.5 mm to about 1 mm in some embodiments.

Figure 7:
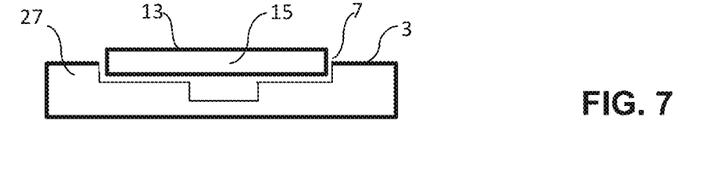
FIG. 7 schematically illustrates a side view of a slide tray and a microscope slide retained thereon.

It should be understood that a slide inset 7 need only be deep enough to retain a microscope slide in the designated area. As such, it can be shallower than a typical microscope slide thickness (generally about 1 mm). As illustrated in a side view of a slide tray 27 in FIG. 7, in such an embodiment, the upper surface 13 of a microscope slide 15 may extend above the upper surface 3 of the slide tray 27 when the microscope slide 15 is retained in the slide inset 7. Of course, a slide inset can be the same depth as the microscope slide, such that the surfaces are coplanar or can be deeper such that the surface of the microscope slide is below the surface of the slide tray.

Figure 8:
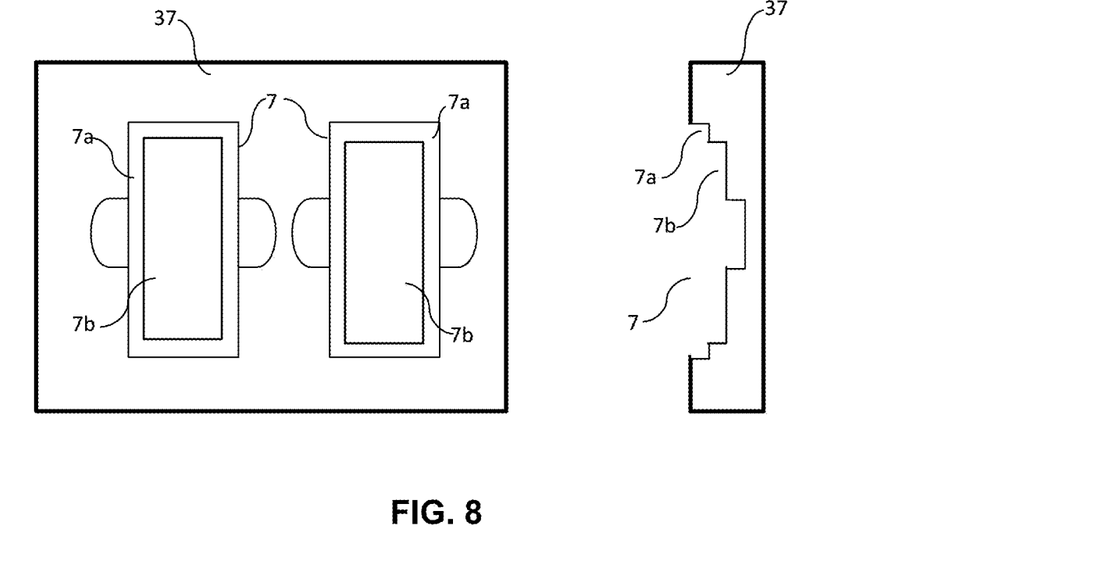
FIG. 8 schematically illustrates a top view and a side view of one embodiment of a slide tray.

In one embodiment a single slide inset can be configured to retain microscope slides of different sizes. FIG. 8 illustrates an example of one such embodiment in a top view (left) and a side view (right). As seen in FIG. 8, a slide tray 37 defines two slide insets 7. Each slide inset 7 further defines a first inset 7a and a second nested inset 7b that is deeper than the first inset 7a. The first inset 7a can thus be sized to retain a microscope slide of a first size, and the second inset 7b can be sized to retain a microscope slide of a second, smaller size.

Figure 9:
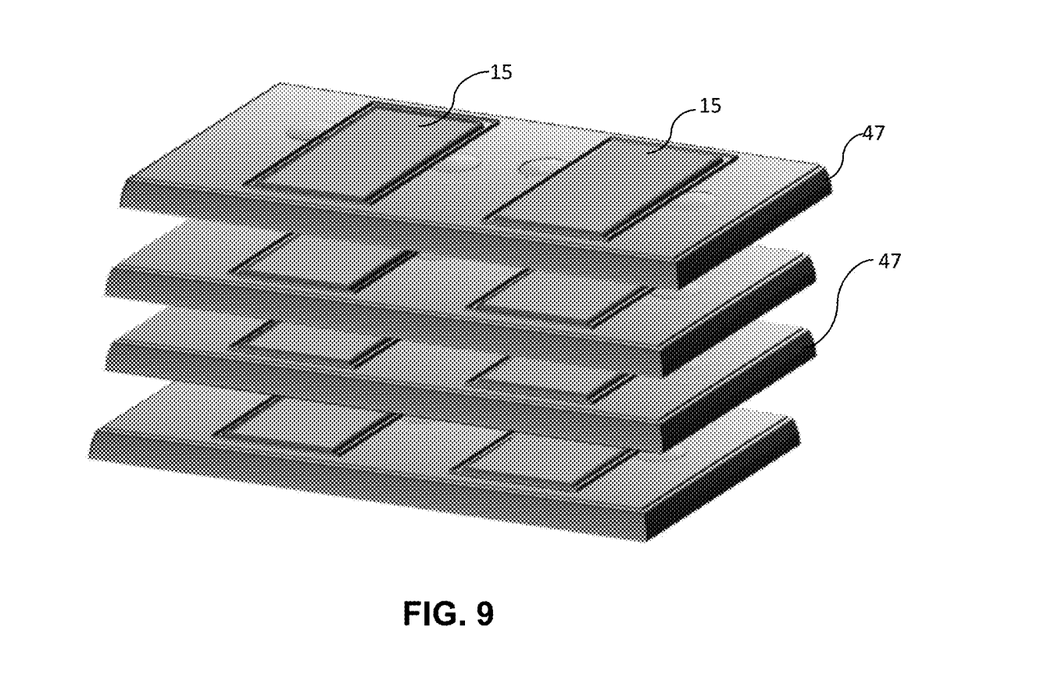
FIG. 9 schematically illustrates another embodiment of a tray stack including a plurality of vertically stacked slide trays.

FIG. 9 illustrates another embodiment of a slide tray 47. As illustrated, the dimensions of the slide tray 47 are somewhat different than the dimensions of the slide tray 17 of FIG. 5 and the slide tray 27 of FIG. 6. The particular dimensions of any slide tray can be varied according to the size of the bench top incubator, the number of tray stacks to be included in the incubator, the number of slides to be retained on each slide tray, the bracket system used to retain the slide tray within the chamber, the materials of construction, etc. as is known in the art.

According to one embodiment, the slide insets of a slide tray can optionally include access insets that can ease placing and removal of slides from a slide tray. For example, and as illustrated in FIG. 5-FIG. 9, the individual slide insets can include access insets on either side of the slide inset. With particular reference to FIG. 6, a slide inset 7 can include a first access inset 8 and a second access inset 9 located on opposite sides from one another of the slide inset 7. The access insets 8, 9 can have any suitable shape and depth so as to allow an individual to grasp a microscope slide retained in the slide inset 7. For example, in the illustrated embodiment, the access insets 8, 9 have a generally semi-circular cross section, but this is not a requirement of the devices, and any suitable shape can be utilized.

As shown in the side view of FIG. 6, the access inset 9 can generally be slightly deeper than the slide inset 7, as this can aid in grasping a slide retained in the slide inset 7. By way of example, an access inset 8, 9, can generally have a depth within a slide tray of about 2 mm or less, for instance from about 1 mm to about 2 mm or about 1.5 mm in some embodiments.

Figure 10:
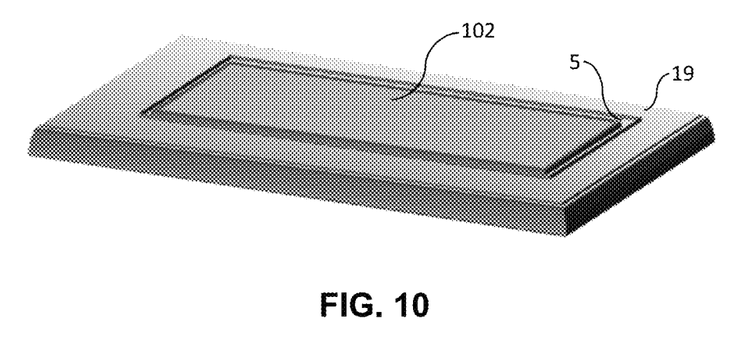
FIG. 10 schematically illustrates one embodiment of a plate tray.

Referring again to FIG. 2, a bench top incubator 10 can include a second tray stack 18 that includes a plurality of plate trays 19. FIG. 10 illustrates one embodiment of a plate tray 19 as may be incorporated in a bench top incubator. As illustrated, a plate tray 19 can include a plate inset 5 configured to retain a multi-well plate 107 therein.

A plate tray can be formed of similar materials as a slide tray, or of different materials, as desired. In some embodiments, a plate tray 19 can have somewhat larger dimensions than a slide tray, but this is not a requirement of a bench top incubator, and is generally due to the fact that the multi-well plates retained in a plate tray tend to be larger than the slides retained in a slide tray. In addition, a plate tray can generally be held in a chamber 14 of an incubator 10 by use of a similar bracket system as is utilized to retain the slide trays therein. This is not a requirement of an incubator, but the system should allow for access to the multi-well plates held within the incubator.

Figure 11:
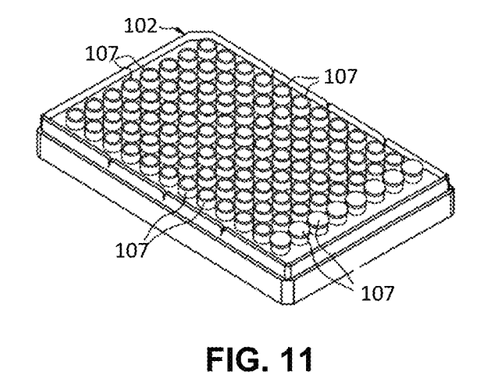
FIG. 11 schematically illustrates a multi-well plate as may be retained on a plate tray.

FIG. 11 illustrates a typical multi-well plate 102 as may be retained by use of a plate tray. In this particular embodiment, the multi-well plate 102 is a 96-well plate that defines 96 individual wells 107 as shown. Each well 107 includes a rim, sidewalls, and a bottom according to standard practice. The wells 107 are generally arranged in a matrix of mutually perpendicular rows and columns. For example, the multi-well plate 102 can include a matrix of wells 107 having dimensions of 4×6 (24 wells), 8×12 (96 wells) or 16×24 (384 wells).

While the plate tray 19 illustrated in FIG. 10 is designed to retain a single multi-well plate 102, the disclosed incubators are not limited to this design, and in other embodiments, a plate tray may be designed to retain multiple plates. The preferred number of multi-well plates to be retained on a single plate tray can generally depend upon the size of the incubator and the size of the multi-well plates to be retained. In addition, a plate tray can include a series of nested plate insets, similar to the nested slide insets described above, so as to be configured to retain multi-well plates of various sizes.

Figure 12:
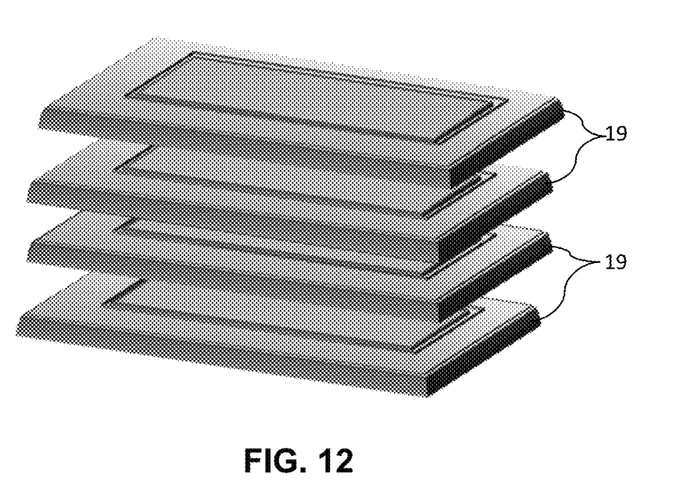
FIG. 12 schematically illustrates one embodiment of a tray stack including a plurality of vertically stacked plate trays.

FIG. 12 demonstrates a tray stack of four multi-well plate trays 19 as may be included in a bench top incubator. Through utilization of a suitable bracket system, for instance as described previously, each plate tray 19 can be individually accessed during use of the bench top incubator.

In operation, an operator can place a slide and/or a multi-well plate carrying a sample onto a tray in the incubator. Any biological sample obtained from any source is encompassed herein, though, as stated previously, the bench top incubator is generally not designed for use in live cell incubations. Beneficially, as the bench top incubator is not intended for incubation of living cells, it can be of a simpler design. For example, the bench top incubator need not include gas flow and isolation systems for, e.g., $CO_2$ control. In addition, the bench top system can be a non-sterile system and as such need not include materials and devices to insure sterility of a sample, as it is generally intended for use in incubation of non-sterile biological samples.

A sample can be pre-processed according to methodology as is known in the art prior to placement on a slide or into a multi-well plate. Beneficially, the bench top incubator can be utilized with a single sample, multiple different samples or a plurality of identical samples. For instance, a biological sample derived from a first source can be located in a multi-well plate and a biological sample derived from a second source can be located in a different multi-well plate or on a slide and both can be placed in the incubator for thermal incubation or controlled standard temperature (e.g., 25° C.) incubation. Similarly, multiple different plates/slides can carry samples obtained from the same source, but the samples can be pre-processed according to different methodologies.

Another of the benefits of the bench top incubator is the capacity of the incubator for a large number of slides and multi-well plates. For instance, should a protocol call for the incubation of a large number of slides, the plate trays or the plate tray brackets can be utilized to carry slide trays, thereby increasing the capacity of the incubator for additional slides. Moreover, and depending upon the relative size of the slide trays and the plate trays, in one embodiment additional plate trays can be retained on unused slide trays or by use of slide tray brackets, thereby increasing the multi-well plate capacity of the incubator.

Following placement of the sample(s) onto the multi-well plate(s) and/or slide(s), an operator can establish the desired temperature of the chamber 14 either prior to or following the insertion of one or more slides and/or multi-well plates on to the respective trays of the incubator. An operator can adjust the controller of the temperature control assembly 54 to the desired temperature by use of an accessible panel of the control assembly 54 as shown. For instance, whenever the internal temperature in the chamber 14 is lower than the desired operating temperature of the incubator 10, the controller can cycle power to the heater to maintain the operating temperature of the chamber 14 within a desired range. As discussed, the data log for each temperature sensor can be obtained in real time or can be stored for later retrieval.

While certain embodiments of the disclosed subject matter have been described using specific terms, such description is for illustrative purposes only, and it is to be understood that changes and variations may be made without departing from the spirit or scope of the subject matter.

What is claimed is:

1. A bench top incubator having an upper surface and a lower surface and defining a vertical direction from the lower surface to the upper surface, the bench top incubator comprising:
    a first tray stack within a first thermally isolated chamber of the bench top incubator, the first tray stack comprising a first series of brackets spaced apart from one another in the vertical direction, the first tray stack having a first width that is perpendicular to the vertical direction;
    a second tray stack horizontally adjacent to the first tray stack within the bench top incubator, the second tray stack comprising a second series of brackets spaced apart from one another in the vertical direction, the vertical distance between adjacent brackets in the second series of brackets being greater than the vertical distance between adjacent brackets in the first series of brackets, the second tray stack having a second width that is perpendicular to the vertical direction, the second width being greater than the first width;
    a first temperature sensor at a first location within the bench top incubator;
    a second temperature sensor at a second location within the bench top incubator;
    a controller in communication with the first temperature sensor and the second temperature sensor,
    a heater and/or a cooler in communication with the controller to generate an incubation temperature within the first thermally isolated chamber of the incubator; and
    a data logger in communication with the first temperature sensor and the second temperature sensor, the data logger comprising a data storage medium, at least one interface, and a first and second channel for communicating with the first and second temperature sensor, respectively; wherein
    the data logger is configured to provide an independent data log for each of the first and second temperature sensors.

2. The bench top incubator of claim 1, the bench top incubator further comprising a plurality of slide trays, the first tray stack being configured to retain the plurality of slide trays in a vertically stacked arrangement, each slide tray being retained by a bracket of the first tray stack.

3. The bench top incubator of claim 1, the bench top incubator further comprising a plurality of plate trays, the second tray stack being configured to retain the plurality of plate trays in a vertically stacked arrangement, each plate tray being removably retained by a bracket of the second tray stack.

4. The bench top incubator of claim 1, wherein the first and second tray stacks are both within the first thermally isolated chamber.

5. The bench top incubator of claim 1, further comprising a second thermally isolated chamber.

6. The bench top incubator of claim 5, the first thermally isolated chamber containing the first tray stack and the first temperature sensor and the second thermally isolated chamber containing the second tray stack and the second temperature sensor.

7. The bench top incubator of claim 1, wherein the data logger is configured for wireless transmission of data from the data logger.

8. The bench top incubator of claim 7, wherein the data logger is configured for wired transmission of data from the data logger.

9. The bench top incubator of claim 1, wherein the controller and the data logger are configured for one or more of timed mode operation, event driven mode operation, and continuous mode operation.

10. A method for incubating a biological sample by use of the bench top incubator of claim 1, the method comprising
    locating a first biological sample in a first slide tray that is configured to be retained on the first tray stack;
    locating a second biological sample in a first plate tray that is configured to be retained on the second tray stack; and
    communicating temperature data from the first temperature sensor to the data logger, this temperature data comprising the temperature of a first area that encompasses the first biological sample;
    communicating temperature data from the second temperature sensor to the data logger, this temperature data comprising the temperature of a second area that encompasses the second biological sample,
    the data logger providing a first data log and a second data log comprising the temperature data from each of the first and second temperature sensors, respectively.

11. The method of claim 10, wherein the first biological sample is retained on a microscope slide and the second biological sample is retained in a multi-well plate.

12. The method of claim 10, further comprising communicating the first data log and the second data log to a location external to the incubator.

13. The method of claim 12, wherein the communication is wireless or wired.

14. The method of claim 12, wherein the the first data log and the second data log each include a representative temperature for each of a plurality of enquiry periods, a maximum temperature for each of the enquiry periods, and a minimum temperature for each of the enquiry periods.

15. The method of claim 10, wherein the first data log and the second data log are developed according to a timed mode operation.

16. The method of claim 10, wherein the first data log and the second data log are developed according to an event driven mode operation.

17. The method of claim 10, wherein the first data log and the second data log are developed according to a continuous mode operation.

* * * * *